(12) United States Patent
Sakai et al.

(10) Patent No.: US 6,476,004 B1
(45) Date of Patent: Nov. 5, 2002

(54) PHARMACEUTICAL COMPOSITION

(75) Inventors: Atsushi Sakai, Fukuoka (JP); Rumiko Masuda, Fukuoka (JP); Tsuneo Fujii, Fukuoka (JP); Tadashi Mishina, Iruma (JP); Kenji Chiba, Iruma (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 09/231,484

(22) Filed: Jan. 14, 1999

Related U.S. Application Data

(63) Continuation-in-part of application No. PCT/JP97/02448, filed on Jul. 15, 1997.

(30) Foreign Application Priority Data

Jul. 18, 1996 (JP) .............................. 8-189380
Jan. 19, 1998 (JP) ............................ 10-008045

(51) Int. Cl.⁷ ..................... A61K 31/715; A61K 31/13; C07C 211/00; C07C 215/00
(52) U.S. Cl. ......................... 514/58; 514/579; 564/463; 564/503
(58) Field of Search ........................... 514/58

(56) References Cited

U.S. PATENT DOCUMENTS

| | | | | |
|---|---|---|---|---|
| 4,727,064 A | * | 2/1988 | Pitha | 514/58 |
| 5,604,229 A | | 2/1997 | Fujita et al. | 514/255 |
| 5,605,892 A | | 2/1997 | Ikejiri | 514/58 |
| 5,663,170 A | | 9/1997 | Ushio et al. | 514/231.2 |
| 5,719,176 A | | 2/1998 | Fujita et al. | 514/440 |

FOREIGN PATENT DOCUMENTS

| | | |
|---|---|---|
| EP | 0 335 545 | 10/1989 |
| EP | 472327 | 2/1992 |
| EP | 627406 A1 | 7/1994 |
| EP | 621036 A1 | 10/1994 |
| EP | 778263 A1 | 11/1997 |
| EP | 812588 A1 | 12/1997 |
| JP | 76/133960 | * of 1976 |
| JP | 58148816 A | 9/1983 |
| JP | 63-253022 | 10/1988 |
| JP | 5213757 | 8/1993 |
| JP | 95/228532 | * of 1995 |
| JP | 95/316065 | * of 1995 |
| JP | 7228532 A | 8/1995 |
| JP | 7316065 A | 12/1995 |
| WO | WO/9408943 | * of 1994 |
| WO | WO 9408943 A1 | 4/1994 |
| WO | WO 9606068 A1 | 2/1996 |

OTHER PUBLICATIONS

K. Chiba et al., "FTY720, A Novel Immunosuppressant Prossessing Unique Mechanisms. I. Prolongation of Skin Allograft Survival and Synergistic Effect in Combination with Cyclosporine in Rats", *Transplantation Proceedings*, vol. 28, No. 2, Apr. 1996, pp. 1056–1059.
Derwent (English Summary) JP 7–316065.
Derwent (English Summary) JP 58–148816.
Derwent (English Summary) JP 60–16547.
Derwent (English Summary) JP 8–175985.
Derwent (English Summary) JP 51–133960.

* cited by examiner

*Primary Examiner*—Johann Richter
*Assistant Examiner*—Howard V. Owens, Jr.
(74) *Attorney, Agent, or Firm*—Crowell & Moring LLP

(57) ABSTRACT

Medicinal compositions which can be processed into solutions and are useful in inhibiting rejection reactions against the transplantation of organs or bone marrow, in the maintenance immunotherapy therefor or in treating autoimmune diseases, characterized by containing 2-amino-2-[2-(4-octylphenyl)ethyl]propane-1,3-diol or pharmaceutically acceptable acid-addition salts thereof and cyclodextrins as a stabilizer optionally together with saccharides, if required.

21 Claims, No Drawings

PHARMACEUTICAL COMPOSITION

This application is a continuation-in-part of PCT/JP97/02448 filed Jul. 15, 1997.

FIELD OF THE INVENTION

The present invention relates to a pharmaceutical composition and composition for kit containing 2-amino-2-[2-(4-octylphenyl)ethyl]propane-1,3-diol or a pharmaceutically acceptable acid addition salt thereof as an active ingredient. More particularly, the present invention relates to a pharmaceutical composition containing 2-amino-2-[2-(4-octylphenyl)ethyl]-propane- 1,3-diol or a pharmaceutically acceptable acid addition salt thereof and a cyclodextrin as a stabilizer, which is suitable for the suppression of rejection in organ (e.g., kidney, liver, heart, small intestine and the like) or bone marrow transplantation, for immunosuppressive sustention therapy or for the treatment of autoimmune diseases, and which can be formulated into a liquid preparation.

BACKGROUND OF THE INVENTION

2-Amino-2-[2-(4-octylphenyl)ethyl]propane-1,3-diol and a pharmaceutically acceptable acid addition salt thereof are known to be useful as a suppressant of rejection in organ or bone marrow transplantation or as a therapeutic agent of various autoimmune diseases such as psoriasis, Behcet's disease and the like and rheumatic diseases, as described in, for example, WO94/08943.

This compound has been developed as a preparation for oral administration. When it is used as a suppressant of the rejection in organ or bone marrow transplantation, its administration immediately after the transplantation is desirable to produce effects as quickly as possible. In consideration of the condition of the patient, however, the administration route should be an injection rather than an oral one. When said compound is used for an eye disease such as Behcet's disease, it needs to be applied in the form of an eye drop.

The above-mentioned WO94/08943 discloses a preparation of said compound as an injection, and the solubilizer therefor disclosed is polyethylene glycol or ethanol. Nevertheless, polyethylene glycol shows undesirable effects such as local irritation and hemolysis, and the use thereof will be limited. In addition, ethanol is unapplicable to injections due to the local irritation it causes.

Moreover, WO97/24112 discloses, as an external preparation of the above-mentioned compound, an eye drop of said compound employed polyoxyethylene hardened castor oil, which is surface active, for a solubilizer.

When the above-mentioned compound, particularly 2-amino-2-[2-(4-octylphenyl)ethyl]propane-1,3-diol hydrochloride (hereinafter sometimes referred to as the present compound through the specification) is dissolved in distilled water, the aqueous solution thereof shows hemolysis and foams by surface active action of the present compound itself. While the present compound is water-soluble, it is problem that the crystalline deposits of the present compound is found in the aqueous solution at a particular concentration by the influence of peculiar dissoluble mechanism of the present compound. As an additive ordinary employed in a liquid preparation such as an injection or an eye drop, an aqueous solution of the present compound added with isotonicity such as sodium chloride and/or solubilizer such as polyoxyethylene hardened castor oil or viscosity-increasing agent such as polyvinylpyrrolidone, possessed the aforementioned problems such as hemolysis, foaming or crystalline deposits, and was not satisfactory.

Japanese Patent Unexamined Publication No. 316065/1995 discloses FR901469 substance preparation containing a cyclodextrin, which is associated with less hemolysis and local irritation. Japanese Patent Unexamined Publication No. 228532/1995 discloses an aqueous liquid preparation containing a cyclodextrin, which is improved water-solubility and water-stability of a water-insoluble pharmaceutical agent, and Japanese patent Unexamined Publication No. 133960/1976 discloses a foam-disappearing method produced by surface active agent characterizing adding a cyclodextrin in an aqueous, industrial surface active agent solution which is foaming.

SUMMARY OF THE INVENTION

In view of the above situation, the present inventors have made intensive studies in an attempt to obtain a pharmaceutical composition containing 2-amino-2-[2-(4-octylphenyl)ethyl]propane-1,3-diol or a pharmaceutically acceptable acid addition salt thereof, which is associated with less side effects such as hemolysis or local irritation, superior to foam-disappearing effect and whose active ingredient compound does not deposit as crystals, and which can be prepared into a liquid preparation such as an injection or an eye drop, and found that the addition of a cyclodextrin achieves the objects, which resulted in the completion of the present invention.

Accordingly, the present invention relates to a pharmaceutical composition containing 2-amino-2-[2-(4-octylphenyl)ethyl]propane-1,3-diol or a pharmaceutically acceptable acid addition salt thereof and a cyclodextrin, which can be easily prepared into a pharmaceutical preparation, which is associated with less side effects such as hemolysis, which causes less local irritation, which is superior to foaming-disappearing effect and whose active ingredient compound does not deposit as crystals, and therefore is suitable for a liquid preparation. In the present invention, it is characteristic that, by adding a cyclodextrin as a stabilizer to 2-amino-2-[2-(4-octylphenyl)ethyl] propane-1,3-diol or a pharmaceutical acceptable acid addition salt thereof, all aforementioned problems are settled at the same time. Particularly, it is characteristic of obtaining a liquid preparation which is superior to foam-disappearing effect and whose the active ingredient compound dose not deposit as crystals. The present invention has also noted that the addition of a sugar selected from monosaccharides, disaccharides and sugar alcohols to said composition results in a liquid composition further improved in local irritation.

The pharmaceutical composition of the present invention contains 2-amino-2-[2-(4-octylphenyl)ethyl]propane-1,3-diol or a pharmaceutically acceptable acid addition salt thereof as an active ingredient, a cyclodextrin, if desired, a sugar, and a conventional, pharmaceutically acceptable carrier or diluent, preferably a carrier or diluent suitable for liquid preparations.

The active ingredient, 2-amino-2-[2-(4-octylphenyl) ethyl]propane-1,3-diol and a pharmaceutically acceptable acid addition salt thereof of the pharmaceutical composition of the present invention can be produced by the method disclosed in WO94/08943. Preferred compound is 2-amino-2-[2-(4-octylphenyl)ethyl]propane-1,3-diol hydrochloride. Examples of other acid addition salt include hydrobromide, sulfate, acetate, fumarate, maleate, benzoate, citrate, malate, methanesulfonate and benzenesulfonate.

2-Amino-2-[2-(4-octylphenyl)ethyl]propane-1,3-diol or a pharmaceutically acceptable acid addition salt thereof is added in a proportion of 0.01–20% by weight, particularly 0.1–10% by weight, of the total weight of the composition.

The cyclodextrin to be used in the present invention is a natural cyclodextrin, a branched cyclodextrin, an alkyl-cyclodextrin or a hydroxyalkyl-cyclodextrin. Specific examples thereof include α-cyclodextrin [e.g., Cerdex A-100, trademark, manufactured by Nippon Shokuhin Kako Co. Ltd.], β-cyclodextrin [e.g., Cerdex B-100, trademark, manufactured by Nippon Shokuhin Kako Co. Ltd.], γ-cyclodextrin [e.g., Cerdex G-100, trademark, manufactured by Nippon Shokuhin Kako Co. Ltd.], dodecakis-2,6-O-methyl- α-cyclodextrin, tetradecakis-2,6-O-methyl-β-cyclodextrin, hexadecakis-2,6-O-methyl- γ-cyclodextrin, tetradecakis-2,6-O-ethyl- β-cyclodextrin, α-cyclodextrin partially etherized with 2-hydroxypropyl, β-cyclodextrin partially etherized with 2-hydroxypropyl (HP-β-CyD, e. g., Cerdex HP-β-CD, trademark, manufactured by Nippon Shokuhin Kako Co. Ltd.) and branched α-cyclodextrin and branched β-cyclodextrin wherein glucose or maltose has been bonded via α-1,6 glucoside bond. These cyclodextrins are added in an amount of 1–50 parts by weight, particularly 10–30 parts by weight, per part by weight of the above-mentioned active ingredient.

The sugar to be used in the present invention is selected from monosaccharides, disaccharides and sugar alcohols, such as glucose, fructose, D-maltose, lactose, sucrose, D-mannitol, D-xylitol and D-sorbitol, which may be used alone or in combination. These sugars are added in an amount of 1–100 parts by weight, particularly 5–80 parts by weight, per part by weight of 2-amino-2-[2-(4-octylphenyl) ethyl]propane-1,3-diol or a pharmaceutically acceptable acid addition salt thereof.

When 2-amino-2-[2-(4-octylphenyl)ethyl]propane-1,3-diol or a pharmaceutical acceptable acid addition salt (particularly hydrochloride) is made an aqueous solution, the solution is observed foaming and shown hemolysis and local irritation at 0.01–20% by weight. When the present compound is made the aqueous solution at a higher concentration than 0.1% by weight, the present compound is dissolved by micellization. On the other hand, in the aqueous solution at a lower concentration than 0.05% by weight, the present compound is dissolved as a solution without micellization. The present compound possesses the peculiar dissoluble mechanism and, by this unique dissoluble mechanism, crystalline deposits is found in the aqueous solution at 0.05–0.1% by weight. The present invention characterizes that, by adding a cyclodextrin to the said aqueous solution, the problems such as foaming, hemolysis and local irritation, as well as prevention of crystalline deposits based on micellization, are settled at the same time.

The preparation form of the pharmaceutical composition of the present invention is liquid, which is specifically an injection, an eye drop, a nasal drop, an ear drop, a transfusion, an oral liquid, a liquid for inhalant, a liquid for lotion and the like, with preference given to an injection (e.g., intravenous, subcutaneous, intramuscular, etc.), an eye drop and a transfusion. These preparation forms are suitably selected according to the diseases to be treated, symptoms thereof, sex and age of the patient, application site and the like, and the preparation is formulated by a method known to those of ordinary skill in the art.

The pharmaceutical composition of the present invention can be placed in the market as a completed liquid preparation or a kit including a powder or a lyophilized product containing an active ingredient and a liquid for dissolution. For example, a solution obtained by dissolving the active ingredient, 2-amino-2-[2-(4-octylphenyl)ethyl]propane-1,3-diol or a pharmaceutically acceptable acid addition salt thereof (particularly hydrochloride) in purified water is sterilized by filtration and filled in vials, then lyophilized in vacuo to give lyophilized products. Separately, an aqueous solution is obtained by dissolving a cyclodextrin to be used in the present invention and a sugar as necessary in distilled water. The above-mentioned lyophilized product may be dissolved in such liquid for dissolution when in use. The liquid for dissolution is used in a 5- to 2000-fold amount (part by weight) relative to 2-amino-2-[2-(4-octylphenyl) ethyl]propane-1,3-diol or a pharmaceutically acceptable acid addition salt thereof. By distilled water is meant here distilled water for injection when an injection is intended. The above-mentioned lyophilized product is generally filled in vials, and after displacement with nitrogen, sealed with a rubber seal and then with an aluminum seal, whereby a long term preservation at room temperature becomes possible. The cyclodextrin and sugar to be added as necessary may be contained in a lyophilized product along with the active ingredient, 2-amino-2-[2-(4-octylphenyl)-ethyl]propane-1, 3-diol or a pharmaceutically acceptable acid addition salt thereof, rather than in a liquid for dissolution as mentioned above. The amount of cyclodextrin is 1–50 parts by weight, particularly 10–30 parts by weight, per part by weight of the above-mentioned active ingredient. The amount of the sugar to be added as necessary is 1–100 parts by weight, particularly 5–80 parts by weight, per part by weight of the above-mentioned active ingredient.

The pharmaceutical composition of the present invention may contain, in addition to the above-mentioned ingredients, solvents, isotonizing agents, pH adjusting agents, buffering agents, antioxidants, thickeners, surfactants, preservatives, moisturing agents, aromatics, coloring agents and the like as appropriate. These additives may be added when preparing the composition of the present invention into a pharmaceutical preparation or may be added to the liquid for dissolution contained in the above-mentioned kit preparation, which is used for dissolution when in use.

The pharmaceutical composition of the present invention can be used in the form of a liquid preparation for the suppression of rejection after organ or bone marrow transplantation, immunosuppressive sustention therapy, and treatment of eye diseases such as Behcet's disease and uveitis, and dermatitis inclusive of psoriasis, atopic dermatitis, contact dermatitis and allergic dermatitis. More specifically, the pharmaceutical preparation of the present invention can be used for the prophylaxis and treatment of various applicable diseases (e.g., immunosuppressant for organ or bone marrow transplantation, various autoimmune diseases, various allergic diseases and the like) conventionally performed with oral preparations.

The composition of the present invention can be used, in the form of a liquid preparation, for the treatment and prophylaxis of resistance or rejection in organ or tissue transplantation (e.g., transplantation of heart, kidney, liver, lung, bone marrow, cornea, pancreas, small intestine, limb, muscle, nervus, fatty marrow, duodenum, skin and pancreatic islet cell, and xeno-transplantation), graft-versus-host (GvH) diseases by bone marrow or small intestine transplantation, autoimmune diseases such as rheumatoid arthritis, systemic lupus erythematosus, nephrotic syndrome lupus, Hashimoto's thyroiditis, multiple sclerosis, myasthenia gravis, type I diabetes mellitus, type II adult onset diabetes mellitus, uveitis, nephrotic syndrome, steroid-dependent and steroid-resistant nephrosis, palmoplantar pustulosis, allergic encephalomyelitis, glomerulonephritis, etc., and infectious diseases caused by pathogenic microorganisms. The composition of the present invention is also useful for treating inflammatory, proliferative and hyperproliferative skin diseases and cutaneous manifestations of immunologically-mediated illnesses such as psoriasis, psoriatic arthritis, atopic eczema (atopic dermatitis), contact dermatitis and further eczematous dermatitises, seborrheic dermatitis, lichen planus, pemphigus, bullous pemphigoid, epidermolysis bullosa, urticaria, angioedemas, vasculitides, erythemas, cutaneous eosinophilias, acne, alopecia areata, eosinophilic fasciitis, and atherosclerosis. More particularly, the composition of the present invention is useful in hair revitalizing, such as in the treatment of female or male pattern alopecia, or senile alopecia, by providing epilation prevention, hair germination, and/or a promotion of hair generation and hair growth.

The composition of the present invention is further useful in the treatment of respiratory diseases, for example, sarcoidosis, fibroid lung, idiopathic interstitial pneumonia, and reversible obstructive airways disease, including conditions such as asthma, including bronchial asthma, infantile asthma, allergic asthma, intrinsic asthma, extrinsic asthma and dust asthma, particularly chronic or inveterate asthma (e.g., late asthma and airway hyperresponsiveness), bronchitis and the like. The composition of the present invention may be also useful for treating hepatic injury associated with ischemia. The composition of the present invention is also applied to certain eye diseases such as conjunctivitis, keratoconjunctivitis, keratitis, vernal conjunctivitis, uveitis associated with Behcet's disease, herpetic keratitis, conical cornea, dystorphia epithelialis corneae, keratoleukoma, ocular pemphigus, Mooren's ulcer, scleritis, Graves' ophthalmopathy, severe intraocular inflammation and the like.

The composition of the present invention is also useful for preventing or treating inflammation of mucosa or blood vessels (e.g., leukotriene B4-mediated diseases, gastric ulcers, vascular damage caused by ischemic diseases and thrombosis, ischemic bowel disease, inflammatory bowel disease (e.g., Crohn's disease and ulcerative colitis), necrotizing enterocolitis), or intestinal lesions associated with thermal burns. The composition of the present invention is further useful for treating or preventing renal diseases including interstitial nephritis, Goodpasture's syndrome, hemolytic uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, vitiligo vulgaris, ichthyosis vulgaris, photoallergic sensitivity and cutaneous T cell lymphoma; circulatory diseases including arteriosclerosis, aortitis, polyarteritis nodos and amyocardosis; collagen disease including scieroderma, Wegener's granuloma and Sjögren's syndrome; adiposis; eosinophilic fasciitis; periodontal disease; nephrotic syndrome; hemolytic uremic syndrome: and muscular dystrophy.

Further, the composition of the present invention is indicated in the prophylaxis and treatment of diseases including intestinal inflammations or allergies such as Coeliac disease, proctitis, eosinophilic gastroenteritis, mastocytosis, Crohn's disease or ulcerative colitis; and food related allergic diseases which have symptomatic manifestation remote from the gastrointestinal tract, for example, migraine., rhinitis and eczema.

The active ingredient of the pharmaceutical composition of the present invention, 2-amino-2-[2-(4-octylphenyl)ethyl]propane-1,3-diol and a pharmaceutically acceptable acid addition salt thereof also have liver regenerating activity and/or activity in promoting hypertrophy and hyperplasia of hepatocytes. Therefore, they are useful for the treatment and prevention of hepatic diseases such as immunogenic diseases (e.g., chronic autoimmune liver diseases including autoimmune hepatitis, primary biliary cirrhosis and sclerosing cholangitis), partial liver resection, acute liver necrosis (e.g., necrosis caused by toxins, viral hepatitis, shock or anoxia), B-virus hepatitis, non-A/non-B hepatitis and cirrhosis.

The composition of the present invention is also indicated for use as antimicrobial composition, and thus may be used in the treatment of diseases caused by pathogenic microorganisms and the like. Further, the composition of the present invention can be used in the prevention or treatment of malignant rheumatoid arthritis, amyloidosis, fulminant hepatitis, Shy-Drager syndrome, pustular psoriasis, Behcet's disease, systemic lupus erythematosus, endocrine ophthalmopathy, progressive systemic sclerosis, mixed connective tissue disease, aortitis syndrome, Wegener's granulomatosis, active chronic hepatitis, Evans syndrome, pollinosis, idiopathic hypoparathyroidism, Addison disease (autoimmune adrenalitis), autoimmune orchitis, autoimmune oophoritis, cold hemagglutinin disease, paroxysmal cold hemoglobinuria, pernicious anemia, adult T cell leukemia, autoimmune atrophic gastritis, lupoid hepatitis, tubulointerstitial nephritis, membranous nephritis, amyotrophic lateral sclerosis, rheumatic fever, postmyocardial infarction syndrome and sympathetic ophthalmitis.

Moreover, the composition of the present invention can be used in combination with other immunosuppressant(s), steroid(s) (e.g., prednisolone, methylprednisolone, dexamethasone, hydrocortisone and the like) or nonsteroidal antiminammatory agent. As the other immunosuppressant, preferred is particularly selected from azathioprine, brequinar sodium, deoxyspergualin, mizoribine, mycophenolate 2-morphorinoethyl, cyclosporin, rapamycin, tacrolimus monohydrate, leflunomide and OKT-3.

While subject to variation depending on the diseases to be treated, symptoms thereof, sex and age of patients, application site and the like, the composition of the present invention can exhibit preferable clinical effects by applying a product containing this compound in a proportion of 0.00001–20% by weight, preferably 0.0001–10% by weight, once to several times (e.g., 2–5 times) a day.

BEST MODE FOR EMBODYING THE INVENTION

The present invention is described in more detail in the following by referring to Examples, Comparative Example and Experimental Examples.

In the following Examples, the proportions are all based on the weight unless otherwise specified and show w/v %. In the Examples, the present compound means 2-amino-2-[2-(4-octylphenyl)ethyl]propane-1,3-diol hydrochloride as mentioned above.

EXAMPLE 1

An injection containing the present compound and having the following formulation is produced.

| | |
|---|---|
| Present compound | 0.1% |
| α-cyclodextrin (trademark Cerdex A-100) | 1.0% |
| D-mannitol | 5.0% |

The above-mentioned composition is dissolved in distilled water for injection to give an injection (total amount 10 ml). Conventional additives such as preservatives can be added as necessary.

EXAMPLE 2

An injection containing the present compound and having the following formulation is produced.

| | |
|---|---|
| Present compound | 0.1% |
| β-cyclodextrin partially etherized with 2-hydroxypropyl (trademark Cerdex HP-β-CD) | 1.0% |
| D-mannitol | 5.0% |

The above-mentioned composition is dissolved in distilled water for injection to give an injection (total amount 10 ml). Conventional additives such as preservatives can be added as necessary.

EXAMPLE 3

An injection containing the present compound and having the following formulation is produced.

| | |
|---|---|
| Present compound | 0.1% |
| α-cyclodextrin (trademark Cerdex A-100) | 1.0% |

The above-mentioned composition is dissolved in distilled water for injection containing conventional additives such as preservatives as necessary. After sterilization by filtration, the total amount of 10 ml is charged in a vial and lyophilized by a conventional method to give an injection.

EXAMPLE 4

An injection containing the present compound and having the following formulation is produced.

| | |
|---|---|
| Present compound | 0.1% |
| β-cyclodextrin partially etherized with 2-hydroxypropyl (trademark Cerdex HP-β-CD) | 1.0% |

The above-mentioned composition is dissolved in distilled water for injection containing conventional additives such as preservatives as necessary. After sterilization by filtration, the total amount of 10 ml is charged in a vial and lyophilized by a conventional method to give an injection.

EXAMPLE 5

An injection containing the present compound and having the following formulation is produced.

| | |
|---|---|
| Present compound | 0.1% |
| β-cyclodextrin partially etherized with 2-hydroxypropyl (trademark Cerdex HP-β-CD) | 2.0% |
| sodium chloride | 0.9% |

The above-mentioned composition is dissolved in distilled water for injection to give an injection (total amount 10 ml). Conventional additives such as preservatives can be added as necessary.

EXAMPLE 6

An eye drop containing the present compound and having the following formulation is produced.

| | |
|---|---|
| Present compound | 0.1% |
| α-cyclodextrin (trademark Cerdex A-100) | 1.0% |
| D-mannitol | 5.0% |

The above-mentioned composition is dissolved in sterile purified water to give an eye drop (total amount 10 ml). Conventional additives such as preservatives can be added as necessary.

EXAMPLE 7

An eye drop containing the present compound and having the following formulation is produced.

| | |
|---|---|
| Present compound | 0.1% |
| β-cyclodextrin partially etherized with 2-hydroxypropyl (trademark Cerdex HP-β-CD) | 1.0% |
| D-mannitol | 5.0% |

The above-mentioned composition is dissolved in sterile purified water to give an eye drop (total amount 10 ml). Conventional additives such as preservatives can be added as necessary.

COMPARATIVE EXAMPLE 1

| | |
|---|---|
| Present compound | 0.1% |

The present compound is dissolved in distilled water for injection to give an injection (total amount 10 ml).

COMPARATIVE EXAMPLE 2

| | |
|---|---|
| Present compound | 0.1% |
| sodium chloride | 0.9% |

The above-mentioned composition is dissolved in distilled water for injection to give an injection (total amount 10 ml).

COMPARATIVE EXAMPLE 3

| | |
|---|---|
| Present compound | 0.1% |
| mannitol | 5.0% |

The above-mentioned composition is dissolved in distilled water for injection to give an injection (total amount 10 ml).

COMPARATIVE EXAMPLE 4

| | |
|---|---|
| Present compound | 0.1% |
| mannitol | 5.0% |
| sodium lauryl sulfate | 1.0% |

The above-mentioned composition is dissolved in distilled water for injection to give an injection (total amount 10 ml).

COMPARATIVE EXAMPLE 5

| | |
|---|---|
| Present compound | 0.1% |
| mannnitol | 5.0% |
| polysorbate 80 | 1.0% |

The above-mentioned composition is dissolved in distilled water for injection to give an injection (total amount 10 ml).

COMPARATIVE EXAMPLE 6

| | |
|---|---|
| Present compound | 0.1% |
| mannitol | 5.0% |
| polyoxyethylene hardened castor oil 60 (HCO-60) | 1.0% |

The above-mentioned composition is dissolved in distilled water for injection to give an injection (total amount 10 ml).

COMPARATIVE EXAMPLE 7

| | |
|---|---|
| Present compound | 0.1% |
| mannitol | 5.0% |
| polyvinylpyrrolidone 12PF | 1.0% |

The above-mentioned composition is dissolved in distilled water for injection to give an injection (total amount 10 ml).

EXPERIMENTAL EXAMPLE 1

Hemolysis Test

The reagent solutions were prepared for the pharmaceutical preparations of Example 1 and Example 2 according to "YAKUAN No. 2" (Test method for topical disorder caused by injection (draft), Jan. 12, 1979, Safety Section, Pharmaceutical Affairs Bureau, Ministry of Health and Welfare), and absorbance at 540 nm was determined according to the method of Inglot et al (Biochem. Pharmacol., vol. 17, p. 269 (1968)). The results reveal that the preparations of Example 1 and Example 2 showed significant decrease in hemolysis. On the contrary, the pharmaceutical preparations of Comparative Example 1–7 showed hemolysis.

EXPERIMENTAL EXAMPLE 2

Local Irritation Test

The pharmaceutical preparation of Example 1 was intravenously administered repetitively to 5 week-old LEW rats for 5 days, and the presence of local irritation was examined using swelling percentage of the tail [(diameter of the tail of the rats administered with drug–diameter of the tail of the control rats) diameter of the tail of the control rats×100] as an index. As a result, the percentage was 0% in Example 1, thus showing the absence of local irritation caused by the preparation of Example 1.

EXPERIMENTAL EXAMPLE 3

Crystalline Deposit Test

The preparation of example 1 or 2 was filtered under an aseptic condition, and filled up into an ampul, then fused, followed by sterilizing under heating at 121° C. for 20 minutes to prepare an injection (total amount 2 ml). When these preparations were allowed to stand at room temperature for an hour, it was confirmed that crystalline deposits were not observed in the preparations of example 1 and 2. Moreover, when the preparation of example 1 or 2 was allowed to stand for a week in a refrigerator, crystalline deposits were not observed in both preparations. On the contrary, crystalline deposits is found in the preparations of Comparative Example 1, 2, 3, 4 and 7 at room temperature and in cold storage.

EXPERIMENTAL EXAMPLE 4

Foaming Test

The operation that an ampul is stood erect, laid down, and then stood erect again, is counted as one time. When this operation is repeated ten times, foaming produced is disappeared within a minutes in the preparations of example 1 and 2, and it is confirmed that foam-disappearing time is short remarkably. On the contrary, foaming produced in the preparations of Comparative Example 1–7 is not disappeared not less than five minutes.

A pharmaceutical composition suitable for a liquid preparation, which contains 2-amino-2-[2-(4-octylphenyl)ethyl]-propane-1,3-diol or a pharmaceutically acceptable acid addition salt thereof, which composition being associated with less local irritation and side effects such as hemolysis, superior to foaming-disappearing effect and whose active ingredient compound does not deposit as crystals, and capable of being formulated into a pharmaceutical preparation with ease, can be provided by adding a cyclodextrin as a stabilizer. The local irritation can be more decreased by adding a sugar to the composition.

What is claimed is:

1. A pharmaceutical compositions comprising:
    2-amino-2-[2-(4-octylphenyl)ethyl]propane-1,3-diol or a pharmaceutically acceptable acid addition salt thereof as an active ingredient;
    a cyclodextrin; and a pharmaceutically acceptable carrier or diluent, wherein the active ingredient is contained in a proportion of 0.05–0.1% by weight in the composition, wherein said active ingredient is soluble in water at concentrations below 0.05% by weight and above 0.1% by weight, but has a tendency to form crystalline deposits from an aqueous solution upon standing only when dissolved in a proportion of 0.05–0.1% by weight, and wherein said cyclodextrin prevents said crystalline deposits from forming.

2. The pharmaceutical composition of claim 1, wherein the cyclodextrin is a member selected from the group consisting of natural cyclodextrins, branched cyclodextrins, alkyl-cyclodextrins and hydroxyalkyl-cyclodextrins.

3. The pharmaceutical composition of claim 1, wherein the cyclodextrin is contained in a proportion of 1–50 parts by weight per part by weight of the active ingredient.

4. The pharmaceutical composition of claim 1, further comprising a sugar.

5. The pharmaceutical composition of claim 4, wherein the sugar is a member selected from the group consisting of monosaccharides, disaccharides and sugar alcohols.

6. The pharmaceutical composition of claim 4, wherein the sugar is one or more members selected from the group consisting of D-mannitol, glucose, D-xylitol, D-maltose, D-sorbitol, lactose, fructose and sucrose.

7. The pharmaceutical composition of claim 4, wherein the sugar is contained in a proportion of 1–100 parts by weight per part by weight of the active ingredient.

8. The pharmaceutical composition of claim 1, wherein the cyclodextrin is contained in a proportion of 1–50 parts by weight per part by weight of the active ingredient.

9. The pharmaceutical composition of claim 1, which is associated with less hemolysis or local irritation, or superior to foam-disappearing effect.

10. A method for preventing crystalline deposits of 2-amino-2-[2-(4-octylphenyl)ethyl]propane-1,3-diol or a pharmaceutically acceptable acid addition salt thereof, wherein said 2-amino-2-[2-(4-octylphenyl)ethyl]propane-1,3-diol and said pharmaceutically acceptable acid addition salt thereof are soluble in water at concentrations below 0.05% by weight and above 0.1% by weight, but have a tendency to form crystalline deposits from an aqueous solution upon standing only when dissolved in a proportion of 0.05–0.1% by weight of the composition, said method comprising adding a cyclodextrin to a composition comprising 0.05–0.1% by weight of said 2-amino-2-[2-(4-octylphenyl)ethyl]propane-1,3-diol, in prophylaxis or treatment of suppression of rejection, autoimmune diseases, or allergic diseases.

11. A method for lessening hemolysis or local irritation of 2-amino-2-[2-(4-octylphenyl)ethyl]propane-1,3-diol or a pharmaceutically acceptable acid addition salt thereof, wherein said 2-amino-2-[2-(4-octylphenyl)ethyl]propane-1, 3-diol and said pharmaceutically acceptable acid addition salt thereof are soluble in water at concentrations below 0.05% by weight and above 0.1% by weight, but have a tendency to form crystalline deposits from an aqueous solution upon standing only when dissolved in a proportion of 0.05–0.1% by weight of the composition, said method comprising adding a cyclodextrin to a composition comprising 0.05–0.1% by weight of said 2-amino-2-[2-(4-octylphenyl)ethyl]propane-1,3-diol, in prophylaxis or treatment of suppression of rejection, autoimmune diseases, or allergic diseases.

12. The method of claim 11, wherein the 2-amino-2-[2-(4-octylphenyl)ethyl]propane-1,3-diol or pharmaceutically acceptable acid addition salt thereof is in the form of an aqueous dispersion.

13. A kit comprising a pharmaceutical composition according to claim 1.

14. A kit according to claim 13, comprising:

a lyophilized product of 2-amino-2-[2-(4-octylphenyl) ethyl]propane-1,3-diol or a pharmaceutically acceptable acid addition salt thereof, and a liquid for dissolution comprising an aqueous solution containing a cyclodextrin.

15. A kit according to claim 13, comprising:

a lyophilized product containing 2-amino-2-[2-(4-octylphenyl)ethyl]propane-1,3-diol or a pharmaceutically acceptable acid addition salt thereof;

a cyclodextrin; and a liquid for dissolution containing distilled water.

16. A kit according to claim 14, wherein the cyclodextrin is contained in a proportion of 1–50 parts by weight per part by weight of the lyophilized product.

17. A kit according to claim 15, wherein the cyclodextrin is contained in a proportion of 1–50 parts by weight per part by weight of the lyophilized product.

18. A kit according to claim 14, wherein the sugar is further added to either the lyophilized product or the liquid for dissolution.

19. A kit according to claim 15, wherein the sugar is further added to either the lyophilized product or the liquid for dissolution.

20. A kit according to claim 15, wherein the sugar is contained in a proportion of 1–100 parts by weight per part by weight of the active ingredient.

21. The method of claim 10, wherein the active ingredient compound is in the form of an aqueous solution.

* * * * *